United States Patent [19]

Mihalow

[11] 4,365,896
[45] Dec. 28, 1982

[54] OPTICAL ATTENUATION MONITOR SYSTEM AND METHOD

[75] Inventor: Frederick A. Mihalow, Allentown, Pa.

[73] Assignee: Bethlehem Steel Corp., Bethlehem, Pa.

[21] Appl. No.: 136,847

[22] Filed: Apr. 3, 1980

[51] Int. Cl.³ ............................................. G01N 21/47
[52] U.S. Cl. ................................... 356/446; 356/239; 356/341
[58] Field of Search ................. 356/38, 237, 239, 240, 356/338, 341, 342, 446, 448, 447; 250/223 B

[56] References Cited

U.S. PATENT DOCUMENTS

| | | | |
|---|---|---|---|
| 2,215,211 | 9/1940 | Derol | 356/448 |
| 3,328,587 | 6/1967 | Brown et al. | 356/338 |
| 3,392,623 | 7/1968 | Walker et al. | 356/434 |
| 3,693,025 | 9/1972 | Brunton | 356/446 |
| 3,734,626 | 5/1973 | Roberts et al. | 356/371 |
| 3,761,724 | 9/1973 | Dennis | 356/434 |
| 3,892,485 | 7/1975 | Merritt et al. | 356/339 |
| 3,894,806 | 7/1975 | Remy et al. | 356/240 |
| 3,952,196 | 4/1976 | Larsen | 250/372 |
| 3,988,068 | 10/1976 | Sprague | 356/239 |
| 4,027,982 | 7/1977 | Ohishi | 356/237 |

Primary Examiner—R. A. Rosenberger
Attorney, Agent, or Firm—George G. Dower; Joseph J. O'Keefe; Michael J. Delaney

[57] ABSTRACT

Light operative apparatus is located inside electro-optical instrument viewing window, such as that used by a radiation pyrometer or dimensional gage in a steel mill environment, to detect and compensate for optically attenuating objects which may accumulate on the outside surface of the viewing window. Light beam irradiates viewing window from inside and optics collects light radiation backscatter which varies as a function of light-scattering attenuating objects that have accumulated on the viewing window outside surface. A light backscatter detector feeds display, alarm and instrument compensation functions.

26 Claims, 5 Drawing Figures

OPTICAL ATTENUATION MONITOR SYSTEM AND METHOD

BACKGROUND OF THE INVENTION

1. Field of the Invention

This invention relates broadly to a radiation detection apparatus and method. More particularly, it relates to an optical attenuation monitor system and method which employs light irradiation techniques to detect accumulation of optically attenuating objects on the outside surface of an electro-optical instrument housing viewing window. The term "light radiation" used herein refers to the visible, infrared and ultraviolet light regions of the electromagnetic radiation spectrum.

2. Description of the Prior Art

In metals producing and rolling mill installations it is commonplace to encounter severe dusty and dirty environments where reliable measurements should be made by electro-optical instruments associated therewith. Because of increased automation and production speed there is an ever increasing need for more accurate and reliable product temperature and dimensional measurements that must be made in these severe environments.

Generally, such measurements are made by electro-optical instruments located in a suitable housing behind a viewing window. For example, light radiation must pass through the viewing window in the form of variable intensity beam to a radiation pyrometer or as a variable image pattern to an electro-optical dimensional gage inside the housing which measures the temperature or dimension of the product located outside of the instrument housing. Invariably, light-scattering optically attenuating objects, such as dust, dirt, scale, pits and scratches, will accumulate on the outside surface of the viewing window. This accumulation attenuates light radiation transmitted through the window and produces an unaccountable optical error which reduces the accuracy and reliability of readings of precision electro-optical instruments located inside the instrument housing.

Heretofore, the outside surface condition of an instrument housing viewing window was either ignored, overlooked or corrected only by routine maintenance of the associated production facility. In a few instances when the viewing window was cleaned, it was done improperly leaving some of the light-scattering optically attenuating objects on the viewing window. An alternative to these procedures is to require more extensive maintenance on a more frequent basis. Until now this would be the recommended procedure because the precision electro-optical instruments inside the housing have no way of knowing about or correcting for optical attenuation errors due to accumulation on the outside of the viewing window.

SUMMARY OF THE INVENTION

A main object of this invention is to provide an optical attenuation monitor system and method that will overcome the foregoing difficulties.

One other object of this invention is to provide a system and method for monitoring optical attenuation of a viewing window in an instrument housing.

Another object of this invention is to provide a system and method for monitoring deviation of optical attenuation of an instrument viewing window from a reference value thereof.

Still another object of this invention is to provide a system and method for monitoring optical attenuation of an instrument viewing window which assures that accurate measurements are being made, yet concurrently permits window maintenance to be carried out on an as-required basis rather than on a more frequent fixed schedule.

The foregoing objects may advantageously be achieved by using optical attentuation monitor apparatus located inside the instrument housing which operates on the principle of irradiating the viewing window with a light beam of radiant energy and detecting the radiant energy backscattered by the light-scattering optically attenuating objects such as dust, dirt, scale, pits and scratches which accumulate on the outside surface of the viewing window. The monitor apparatus includes backscatter radiation detector means having an output signal that varies as a function of the variable optical attenuation, or alternatively, the ratio of optical attenuation and a predetermined value thereof. The output signal is used to drive an optical attenuation display, an optical attenuation alarm for signalling when window maintenance is required, or an optical attenuation correcting circuit for automatically correcting an electro-optical instrument in the housing or an external process controller.

DESCRIPTION OF THE PREFERRED EMBODIMENTS

Referring now to the drawings, in each FIG. 1 to 5 embodiment there is shown an electro-optical instrument 10, such as a radiation pyrometer or electro-optical dimensional gage, located inside an instrument housing not shown. Instrument 10 is aimed, along axis 11, through radiation transmissive viewing window 12 shown in enlarged cross-section and also located in the instrument housing not shown. Viewing window 12 has inside and outside surfaces 13, 14. It is the condition of outside surface 14 of viewing window 12 that must be determined because of the accumulation of light-scattering optically attenuating objects 15, such as dust, dirt, scale, pits and scratches which are experienced in a severe steel mill environment.

A column of unattenuated radiation 16, representing the temperature or dimension of a steel mill product outside of the instrument housing, becomes a column of attenuated radiation 17 when it is conducted through light-scattering optically attenuating objects 15, window 12 and along aiming axis 11. Instrument 10 responds directly to the column of attenuated radiation 17. The difference between column 17 and the column of unattenuated radiation 16 is the optical error which changes the accuracy of electro-optical instrument 10 as a function of accumulation of optical attenuation objects 15 on the outer surface 14 of viewing window 12.

The choice as to which FIGS. 1 to 5 embodiment is utilized to determine the condition of outer surface 14 will depend upon space availability inside the instrument housing, not shown, and to the extent to which optical error detection, and correction, is to be made.

Figure 1:
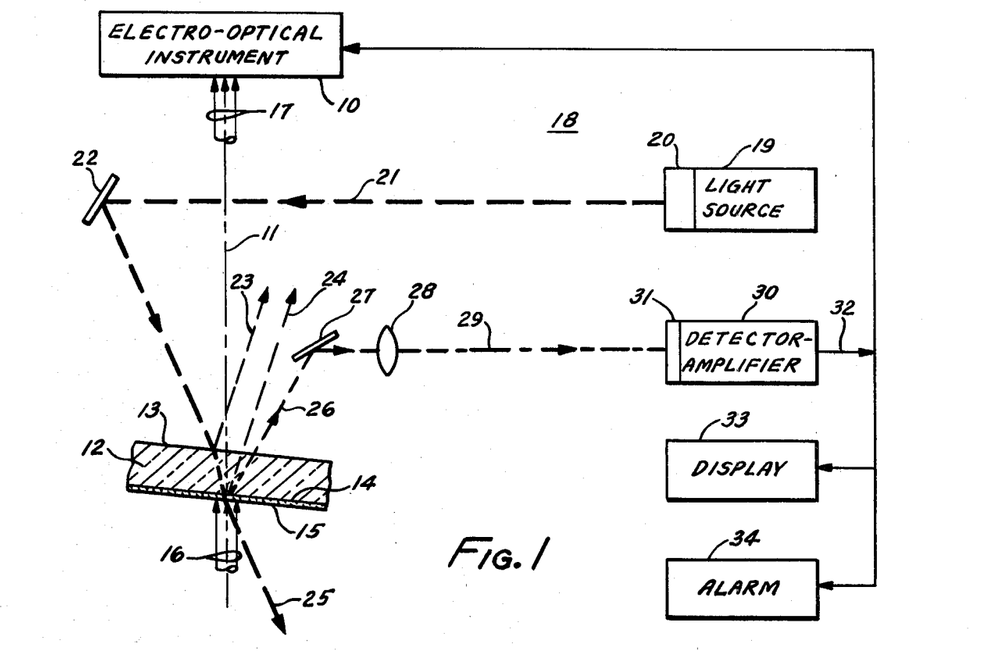
FIG. 1 is a block diagram of a basic optical attenuation monitor system of the present invention.

FIG. 1 shows a basic optical attenuation monitor system 18. Included in monitor system 18 is a light radiation source 19 which produces either a steady or pulsed, collimated, monochromatic source of visible or invisible radiant energy. This may be obtained from, for example, a helium-neon laser source having a wavelength band similar to that of the column of attenuated radiation 17. Light source 19 is optically coupled to a beam expander 20 and produces a main light beam of radiation 21 which is reflected off mirror 22 to radiate viewing window 12. Beam expander 20 can be used to increase the irradiated area of viewing window 12 to the same area as used by the column of attenuated radiation 17.

When irradiating viewing window 12, main light beam of radiation 21 produces parallel primary and secondary reflected light beams 23, 24 when reflecting off of viewing window inner and outer surfaces 13, 14, respectively, as well as a refracted main light beam of radiation 25. These reflected and refracted light beams 23, 24, 25 are unwanted radiation in this invention and are therefore misdirected off the aiming axis 11 so as not to effect a radiation sensing device in instrument 10. The misdirection of unwanted light beams 23, 24, 25 is accomplished by tilting viewing window 12 in one plane, as shown, or a plane orthogonal thereto, or in two orthogonal planes, and selecting a proper angle of incidence of the main light beam of radiation 21 upon viewing window 12, all with reference to aiming axis 11.

Thus, the only remaining light radiation available for use in this invention is light radiation backscatter 26. This has the same wavelength as light source 19 and is produced proportional to the accumulation of optically attenuating objects 15 on the outer surface 14 of viewing window 12. Light radiation backscatter 26 is collected by mirror 27, and focusing lens 28 to form a variable-intensity backscatter beam 29 which varies as a function of the amount of optically attentuating objects 15 on viewing window outer surface 14.

Light radiation backscatter beam 29 is directed upon light radiation detector means, such as a conventional detector-amplifier 30. Device 30 may include electronic filter circuits for responding only to a steady light source 19, or to the frequency of a pulsed light source 19, if electrical and/or magnetic fields of interfering strength are present in the surrounding environment. Synchronous detection may also be used to discriminate against high ambient light levels. Similarly, device 30 may be coupled with an optical filter 31 to pass only radiant energy of the same wavelength as light source 19 if unwanted optical radiation is present. Otherwise, detector-amplifier 30 will produce an output signal 32 which varies as a function of the intensity of light radiation backscatter beam 29, this function relating to the amount of light-scattering optically attentuating objects 15 accumulated on viewing window outer surface 14.

The output signal 32 from light radiation detector-amplifier 30 is fed to display device 33 and alarm device 34. Display device 33 indicates the magnitude of optical attenuation error that will be experienced by electro-optical instrument 10 if not corrected. Alarm device 34 is set to become activated at a preset level of optical attenuation error. Output signal 32 is also fed to electro-optical instrument 10 to automatically compensate for the amount of optical attenuation error contained in the column of attenuated radiation 17 to which instrument 10 is responsive. It is contemplated that output signal 32 may be fed to a computer, not shown, for the same optical attenuation error-correction purpose.

Turning now to FIGS. 2 to 5, there are shown more precise optical attenuation monitor systems which are used whenever a tendency for the light source to drift would affect their accuracy. These systems utilize a reference light beam to compare with the light radiation backscatter beam developed in FIG. 1 to produce a ratio output signal representative of deviation of viewing window outer surface condition from a predetermined value established by the reference beam. The reference beam is obtained from the same light source as the main light beam of radiation and compared either alternately or continuously with the light radiation backscatter beam in either single or dual radiation detector means, respectively.

Each of the FIGS. 2 to 5 optical attenuation monitor systems use many of the same components as the FIG. 1 monitor system 18. These common components are identified with the same reference numerals in FIGS. 2 to 5 as are used in FIG. 1. Therefore, the description of the common components will not be repeated below. Only the new components will be described below.

Figure 2:
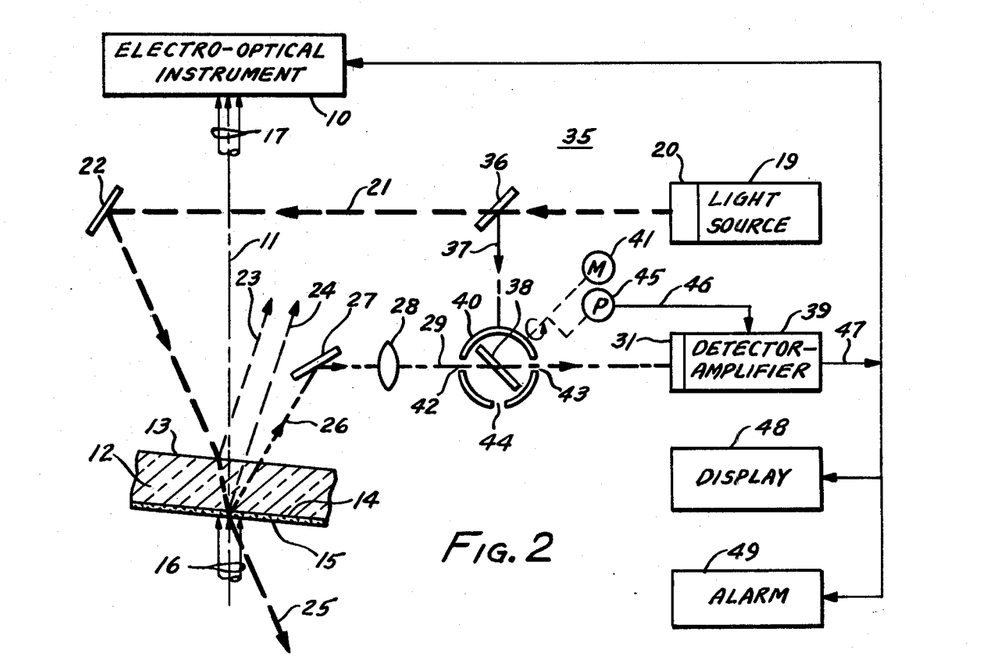
FIGS. 2 to 5 are block diagrams of different embodiments of an optical attenuation monitor system which determines deviation in optical attenuation of the viewing window in an instrument housing from a predetermined value thereof.

FIG. 2 illustrates optical attenuation monitor system 35 for determining deviation in viewing window outer surface 14 condition from a predetermined value thereof. Beam splitter 36 divides the light radiation energy from source 19 into a main light beam of radiation 21 and a reference light beam 37 from a minor portion of the main light beam of radiation 21. Light radiation from backscatter beam 29 is alternately combined in a second beam splitter 38 with reference light beam 37 to alternately direct these two sources of light radiation to detector-amplifier 39.

Rotary chopper 40 driven by motor 41 is shown illustratively to function as an optical switch to alternately select light radiation backscatter beam 29 source or reference light beam 37 source to be directed to detector-amplifier 39. As shown in FIG. 2, rotary chopper 40 blocks reference beam 37 from being combined in beam splitter 38. Light radiation backscatter beam 29 image is directed through light port 42, beam splitter 38 and light port 43 to detector-amplifier 39 while the reference light beam 37 is blocked. When rotary chopper 40 turns counter-clockwise 90°, reference light beam 37 enters light port 43 and beam splitter 38 exits the reference light beam 37 through light port 44 to detector-amplifier 39 while light radiation backscatter beam 29 is blocked. Motor 41 continues to drive rotary chopper 40 to the starting position shown in FIG. 2.

A position encoder 45 is driven by rotary chopper 40 to generate position signal 46 which is used in detector-amplifier 39 for a synchronizing purpose described below. An electro-optical switch with a position output signal may be substituted for rotary chopper 40 and position encoder 45.

Detector-amplifier 39 is a modified version of detector-amplifier 30 in that it is adapted to alternately receive first the light radiation backscatter beam 29, then the reference light beam 37, and develop a ratio output signal 47 of the two functions in synchronism with the rotary chopper position signal 46. In other words, detector-amplifier 39 includes holding circuits, not shown, alternately selected by position signal 47 to hold separate signals representing the intensities of light radiation backscatter beam 29 and reference light beam 37. Device 39 further includes a divider circuit, not shown, to divide the outputs of the holding circuit to produce ratio output signal 47. Device 39 also includes a reset circuit, not shown, to reset the divider and/or holding circuits in synchronism with the rotary chopper position signal 46.

Ratio output signal 47 in FIG. 2 is fed to deviation display device 48 and deviation alarm device 49. Deviation display device 48 indicates the magnitude of optical attenuation deviation error with respect to the reference light beam that will be experienced by electro-optical instrument 10 if not corrected. Deviation alarm device 49 is set to become activated at a preset level of optical attenuation deviation error, also with respect to the reference light beam. Ratio output signal 47 is also fed to electro-optical instrument 10 to automatically correct same for optical attenuation deviation error with respect to the reference light beam. It is also contemplated to feed ratio output signal 47 to a computer, not shown, as an optical attenuation deviation correction signal.

Figure 3:
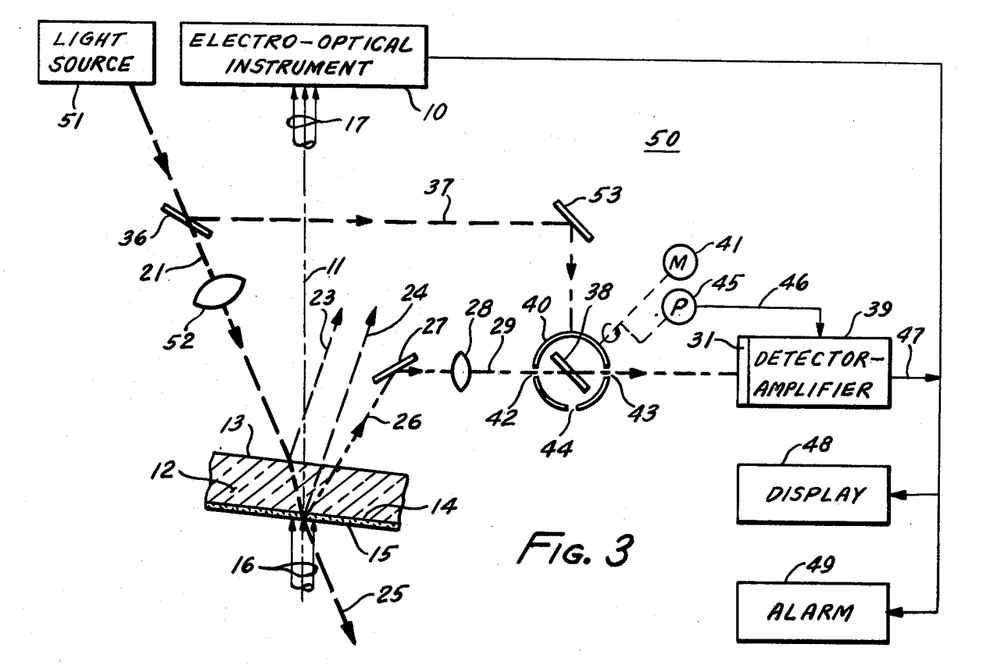

FIG. 3 illustrates optical attenuation monitor system 50 for determining deviation in viewing window outer surface 14 condition from a predetermined value thereof. Monitor system 50 is similar to monitor system 35 in FIG. 2. One difference is in light laser source 51 which is a solid-state device, or alternatively a LED device, having monochromatic visible or invisible radiant energy emitted from a different structure than that of a helium-neon laser in source 19.

Another difference lies in the light radiation generated by light source 51 being aimed through beam splitter 36 to produce the main light beam of radiation 21. Beam 21 is directed through lens 52 and viewing window 12 without the benefit of a mirror as in FIG. 2. The build up of light-scattering optically attenuating objects 15 on window outer surface 14 causes light radiation backscatter beam 29 to form and be imaged alternately through the second beam splitter 38 and rotary chopper 40 on to detector-amplifier 39.

A third difference is characterized by the reference light beam 37, formed by beam splitter 36, being reflected off mirror 53 and also imaged alternately through beam splitter 38 and rotary chopper 40 on to detector-amplifier 39 in synchronism with position signal 46, thereby causing the production of ratio output signal 47 as described above.

Ratio output signal 47 in FIG. 3 is fed to deviation display 48 and deviation alarm 49, and as an optical attenuation deviation error correction signal to electro-optical instrument 10 as described above. Also to a computer not shown.

Figure 4:
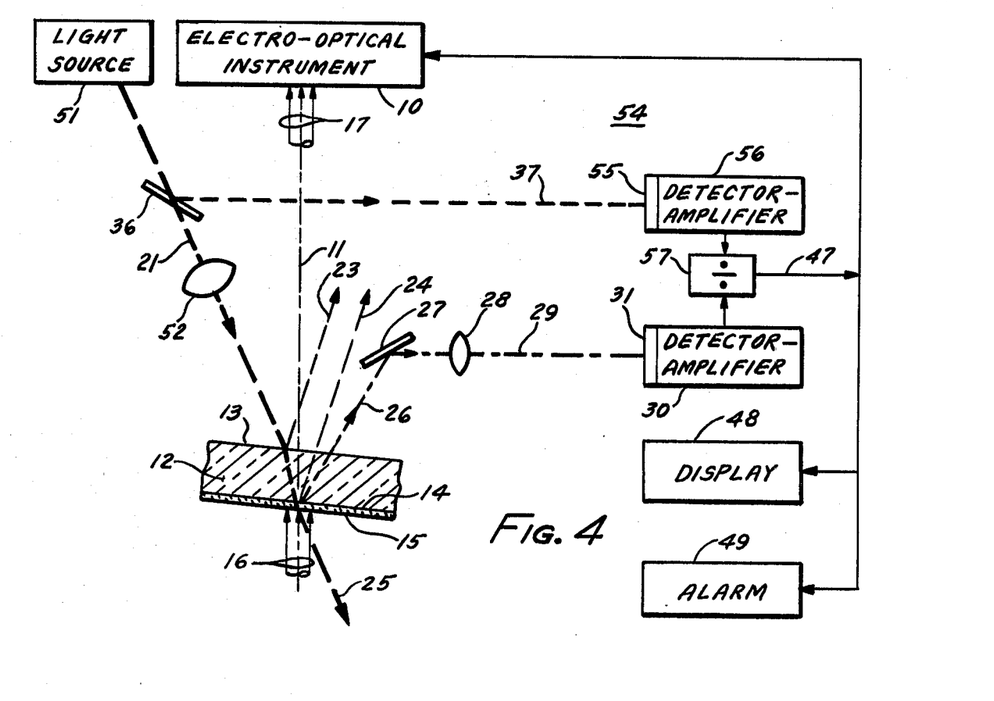

FIG. 4 illustrates optical attenuation monitor system 54 for determining deviation in viewing window outer surface 14 condition from a predetermined value thereof. Optics of monitor system 54 is similar to monitor system 50 shown in FIG. 3, except optical switching for alternately imaging light radiation backscatter beam 29 or reference light beam 37 is replaced by full time dual radiation detector means. More particularly, light radiation backscatter beam 29 is imaged directly through filter 31 and onto detector-amplifier 30, the same as used in monitor system 18 shown in FIG. 1. Reference light beam 37 is imaged directly, rather than through a mirror or beam splitter, through optical filter 55 and onto a second detector-amplifier 56, which device in fact has the same characteristics as detector-amplifier 30. Proportional outputs from detector-amplifiers 30, 56 are fed to divider 57 which produces ratio output signal 47 having characteristics as described above.

Ratio output signal 47 in FIG. 4 is fed to deviation display 48 and deviation alarm 49, and as an optical attenuation deviation error correction signal to electro-optical instrument 10, also to a computer not shown, all as described above.

Figure 5:
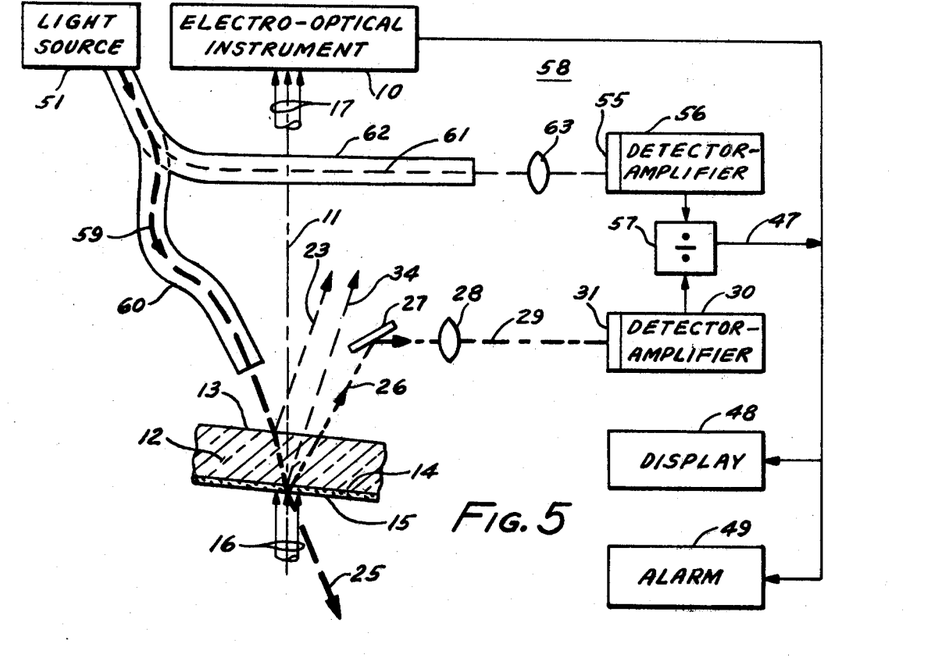

FIG. 5 shows optical attenuation monitor system 58 for determining deviation in viewing window outer surface 14 condition from a predetermined value thereof. Electronics for monitor system 58 are the same as monitor system 54 shown in FIG. 4, but direct-path optics are replaced with flexible path devices. A flexible main light beam of radiation 59 is derived from light source 51 and conducted by fiber optics 60 around a circuitous route to viewing window 12. Light radiation backscatter is collected and beam 29 is imaged directly through filter 31 and onto detector-amplifier 30. Similarly, a flexible reference beam 61 is also derived from laser source 51 and conducted by fiber optics 62 directly through lens 63 and filter 55 onto second detector-amplifier 56. Proportional outputs from detector-amplifiers 30, 56 are fed to divider 57 which produces the ratio output signal 47 having characteristics as described above.

Ratio output signal 47 in FIG. 5 is fed to deviation display 48 and deviation alarm 49, and as an optical attenuation deviation error signal to electro-optical instrument 10, also to a computer, not shown, all as described above.

I claim:

1. Optical attenuation monitor apparatus for determining the surface condition of a radiation transmissive viewing window, comprising:
   (a) means for producing a main light beam of monochromatic radiation and directing same angularly through said window from a first side to a second side where variable light-scattering attenuating objects also collect on the second surface and produce light radiation backscatter of the same wavelength, all reflected and refracted radiation from said main light beam being undetected;
   (b) collecting only the light radiation backscatter from the second side surface through said window and causing same to form a variable-intensity light radiation backscatter beam; and
   (c) light radiation detector means responsive only to the light radiation backscatter beam for producing an output signal that varies as a function of the window second side surface attenuation condition.

2. Optical attenuation monitor apparatus for determining deviation in surface condition of a radiation transmissive viewing window from a predetermined value thereof, comprising:
   (a) means for producing a main light beam of monochromatic radiation and directing same angularly through said window from a first side to a second side where variable light-scattering attenuating objects also collect on the second surface and produce light radiation backscatter of the same wavelength, all reflected and refracted radiation from said main light beam being undetected;
   (b) means for producing a monochromatic reference light beam from a minor portion of the main light beam of radiation;
   (c) collecting only the light radiation backscatter from the second side surface through said window and causing same to form a variable-intensity light radiation backscatter beam; and (d) light radiation detector means responsive only to said light radiation backscatter beam and the reference beam for producing an output signal that varies as the ratio of said two beams, whereby said ratio output signal indicates deviation of said window second side surface attenuation condition from a predetermined value thereof.

3. The apparatus of claim 2 wherein means (c) includes optical switch means for alternately selecting the light radiation backscatter beam or the reference light beam and producing a switch position signal, and detector means (d) is modified to respond alternately to said light radiation backscatter beam or said reference light beam in synchronism with said position signal so as to produce the ratio output signal.

4. The apparatus of claim 2 wherein detector means (d) is modified with separate detector devices to respond simultaneously to a given light radiation backscatter beam and reference light beam, and further modified to include circuit means responsive to the separate detectors for producing said ratio output signal.

5. The apparatus of claim 1 or 2 wherein means (c) includes an optical path having lens means for collecting the backscatter light radiation and producing said light radiation backscatter beam.

6. The apparatus of claim 1 or 2 wherein means (a) includes a beam expander for enlarging the area of impingement of said main light beam upon said window.

7. The apparatus of claim 1 or 2 wherein means (a) includes either a gaseous or a solid state laser source having either a steady or a pulsed output for producing said main light beam of radiation.

8. The apparatus of claim 1 or 2 wherein means (a) includes a mirror for directing the main light beam of radiation onto said window at an angle thereto.

9. The apparatus of claim 2 wherein means (a) includes a beam splitter for dividing a source of radiation into the main light beam of radiation and the reference light beam.

10. The apparatus of claim 2 wherein means (a) further includes a mirror disposed beyond a beam splitter for reflecting either the main light beam of radiation onto said window, or the reference light beam for subsequent use.

11. The apparatus of claim 2 wherein means (a) includes a first beam splitter for dividing a source of radiation into the main light beam of radiation and the reference light beam, and a second beam splitter for combining the reference light beam and the light radiation backscatter beam.

12. The apparatus of claim 11 wherein means (b) further includes optical switch means associated with the second beam splitter for alternately selecting said light radiation backscatter beam or said reference light beam to act on the light radiation detector means.

13. The apparatus of claim 2 wherein means (a) includes first and second fiber optics for flexibly directing respectively the main light beam of radiation to said window and the reference light beam to said light radiation detector means.

14. The apparatus of claim 1 or 2 wherein the light radiation detector means includes an optical filter for passing only the wavelength of the light radiation backscatter.

15. The apparatus of claim 1 or 2 wherein the light radiation detector means includes circuit means to limit detector frequency response to that of either a steady or a pulsed source of light radiation.

16. The apparatus of claim 1 or 2 further including: display means responsive to the light radiation detector means output signal for indicating the amount of viewing window optical attenuation.

17. The apparatus of claim 1 or 2 further including: alarm means responsive to the light radiation detector means output signal for signalling viewing window optical attentuation condition having exceeded a predetermined value.

18. The apparatus of claim 1 or 2 further including: electro-optical means aimed at said window and operative in response to the light radiation detector means output signal to compensate the electro-optical means operation for optical attenuation characteristics of said window.

19. Optical attenuation monitor apparatus for determining the surface condition of a radiation transmissive viewing window, comprising:

(a) means for producing a main light beam of monochromatic radiation including a mirror for directing same angularly through said window from a first side to a second side where variable light-scattering attenuating objects also collect on the second surface and produce light radiation backscatter of the same wavelength, all reflected and refracted radiation from said main light beam being undetected;

(b) collecting only the light radiation backscatter from the second side surface through said window and causing same to form a variable-intensity light radiation backscatter beam;

(c) light radiation detector means responsive only to the light radiation backscatter beam for producing an output signal that varies as a function of the window second side surface attenuation condition; and (d) means responsive to the light radiation detector means output signal and including at least one:
  (1) display means for indicating the amount of window optical attenuation,
  (2) alarm means for signalling window optical attenuation condition having exceeded a predetermined value, and
  (3) electro-optical instrument means aimed at said window and compensated for optical attenuation of said window.

20. Optical attenuation monitor apparatus for determining deviation in surface condition of a radiation transmissive viewing window from a predetermined value thereof, comprising:

(a) means for producing a main light beam of monochromatic radiation including a mirror for directing same angularly through said window from a first side to a second side where variable light-scattering attenuating objects also collect on the second surface and produce light radiation backscatter of the same wavelength, all reflected and refracted radiation from said main light beam being undetected;

(b) means including a beam splitter located ahead of said mirror for producing a monochromatic reference light beam from a minor portion of the main light beam of radiation;

(c) collecting light radiation backscatter from the second side surface through said window and causing same to form a variable-intensity light radiation backscatter beam;
(d) optical switch means including a rotary chopper for alternately selecting the light radiation backscatter beam or the reference light beam, said means also producing a switch position signal;
(e) light radiation detector means responsive alternately to only the light radiation backscatter beam or the reference light beam in synchronism with said position signal for producing an output signal that varies as the ratio of said two beams, whereby the radio output signal indicates deviation of said window second side surface attenuation condition from a predetermined value thereof; and
(f) means responsive to the ratio output signal and including at least one:
  (1) display means for indicating the amount of window optical attenuation,
  (2) alarm means for signalling window optical attenuation condition having exceeded a predetermined value, and
  (3) electro-optical means aimed at said window and compensated for optical attenuation of said window.

21. Optical attenuation monitor apparatus for determining deviation in surface condition of a radiation transmissive viewing window from a predetermined value thereof, comprising:
(a) means including a beam splitter for producing a main light beam of monochromatic radiation and a monochromatic reference light beam from a minor portion of the main light beam of radiation, said main light beam of radiation being directed angularly through said window from a first side to a second side where variable light-scattering attenuating objects also collect on the second surface and produce light radiation backscatter of the same wavelength, all reflected and refracted radiation from said main light beam being undetected;
(b) means including a mirror for directing the reference light beam for subsequent use;
(c) means including a focusing lens for directing only the light radiation backscatter from the second side surface through said window to form a variable-intensity light radiation backscatter beam;
(d) optical switch means including a rotary chopper for alternately selecting the light radiation backscatter beam or the reference light beam, said means also producing a switch position signal;
(e) light radiation detector means responsive alternately to only the light radiation backscatter beam or the reference light beam in synchronism with said position signal for producing an output signal that varies as the ratio of said two beams, whereby the ratio output signal indicates deviation of said window second side surface attenuation condition from a predetermined value thereof; and
(f) means responsive to the ratio output signal and including at least one:
  (1) display means for indicating the amount of window optical attenuation,
  (2) alarm means for signalling window optical attenuation condition having exceeded a predetermined value, and
  (3) electro-optical means aimed at said window and compensated for optical attenuation of said window.

22. Optical attenuation monitor apparatus for determining deviation in surface condition of a radiation transmissive viewing window from a predetermined value thereof, comprising:
(a) means including a beam splitter for producing a main light beam of monochromatic radiation and a monochromatic reference light beam from a minor portion of the main light beam of radiation, said main light beam of radiation being directed angularly through said window from a first side to a second side where variable light-scattering attenuating objects also collect on the second surface and produce light radiation backscatter of the same wavelength, all reflected and refracted radiation from said main light beam being undetected;
(b) collecting light radiation backscatter from the second side surface through said window and causing same to form a variable-intensity light radiation backscatter beam;
(c) light radiation detector means including a first detector responsive only to the light radiation backscatter beam, a second detector responsive only to the reference light beam, and circuit means responsive to both detectors for producing an output signal that varies as the ratio of said two beams, whereby the ratio output signal indicates deviation of said window second side surface attenuation condition from a predetermined value thereof; and
(d) means responsive to the ratio output signal and including at least one:
  (1) display means for indicating the amount of window optical attenuation,
  (2) alarm means for signalling window optical attenuation condition having exceeded a predetermined value, and
  (3) electro-optical means aimed at said window and compensated for optical attenuation of said window.

23. Optical attenuation monitor apparatus for determining deviation in surface condition of a radiation transmissive viewing window from a predetermined value thereof, comprising:
(a) means including first fiber optics for producing a main light beam of monochromatic radiation and flexibly directing same angularly through said window from a first side to a second side where variable light-scattering attenuating objects also collect on the second surface and produce light radiation backscatter of the same wavelength, all reflected and refracted radiation from said main light beam being undetected;
(b) means including second fiber optics for producing a monochromatic reference light beam from the same source as the main light beam of radiation and flexibly directing same for subsequent use;
(c) means including a focusing lens for directing only the light radiation backscatter from the second side surface through said window to form a variable-intensity light radiation backscatter beam;
(d) light radiation detector means including a first detector responsive only to the light radiation backscatter beam, a second detector responsive only to the reference light beam, and circuit means responsive to both detectors for producing an output signal that varies as the ratio of said two beams, whereby the ratio output signal indicates deviation of said window second side surface attenuation condition from a predetermined value thereof; and (e) means responsive to the ratio output signal and including at least one:
   (1) display means for indicating the amount of window optical attenuation,
   (2) alarm means for signalling window optical attenuation condition having exceeded a predetermined value, and
   (3) electro-optical means aimed at said window and compensated for optical attenuation of said window.

24. An optical attenuation monitoring method of determining the surface condition of a radiation transmissive viewing window, which method comprises:
   (a) producing a main light beam of monochromatic radiation;
   (b) directing the main light beam of radiation angularly through said window from a first side to a second side where variable light-scattering attenuating objects also collect on the second surface and produce light radiation backscatter of the same wavelength, all reflected and refracted radiation from said main light beam being undetected;
   (c) collecting only the light radiation backscatter from the second side surface through said window and forming a variable-intensity light radiation backscatter beam; and
   (d) detecting only the light radiation backscatter beam and producing an output signal that varies as a function of the window second side surface attenuation condition.

25. An optical attenuation monitoring method of determining deviation in surface condition of a radiation transmissive viewing window from a predetermined value thereof, which method comprises:
   (a) producing a main light beam of monochromatic radiation;
   (b) producing a monochromatic reference light beam from the same source as the main light beam of radiation;
   (c) directing the main light beam of radiation angularly through said window from a first side to a second side where variable light-scattering attenuating objects also collect on the second surface and produce light radiation backscatter of the same wavelength, all reflected and refracted radiation from said main light beam being undetected;
   (d) collecting only the light radiation backscatter from the second side surface through said window and forming a variable-intensity light radiation backscatter beam; and
   (e) detecting only the light radiation backscatter beam and only the reference light beam and producing an output signal that varies as the ratio of said two beams, whereby said ratio output signal indicates deviation of said window second side surface attenuation condition from a reference value thereof.

26. The method of claim 25 further including the step of alternately selecting the light radiation backscatter beam or the reference light beam before the detecting step and subsequently producing the ratio output signal.

* * * * *

UNITED STATES PATENT AND TRADEMARK OFFICE
CERTIFICATE OF CORRECTION

PATENT NO. : 4,365,896

DATED : December 28, 1982

INVENTOR(S) : Frederick A. Mihalow

It is certified that error appears in the above—identified patent and that said Letters Patent is hereby corrected as shown below:

Claim 20, column 9, line 12, "radio" should read --ratio--.

Claim 23, column 10, subparagraph (c), line 56, delete "means including a focusing lens for directing" and insert --collecting--.

Claim 23, column 10, subparagraph (c), line 58, the words "and causing same" should be inserted after "window".

Signed and Sealed this

Fifth Day of April 1983

[SEAL]

Attest:

GERALD J. MOSSINGHOFF

Attesting Officer

Commissioner of Patents and Trademarks